United States Patent [19]
DePauw et al.

[11] Patent Number: 6,145,668
[45] Date of Patent: Nov. 14, 2000

[54] METHODS AND APPARATUS FOR REMOVING EGGS FROM A MOVING EGG FLAT

[75] Inventors: Daniel T. DePauw, Raleigh; John H. Hebrank, Durham; Robert L. Ilich, Raleigh, all of N.C.

[73] Assignee: Embrex, Inc., Research Triangle Park, N.C.

[21] Appl. No.: 09/226,481

[22] Filed: Jan. 7, 1999

[51] Int. Cl.$^7$ .................................................. A01K 43/04
[52] U.S. Cl. ..................... 209/510; 209/932; 209/912; 209/576; 209/577; 209/644; 209/639
[58] Field of Search ................................ 209/510, 511, 209/640, 932, 912, 577, 576, 587, 643, 644, 639

[56] References Cited

U.S. PATENT DOCUMENTS

| | | | |
|---|---|---|---|
| 3,773,172 | 11/1973 | McClure et al. | 209/73 |
| 3,910,416 | 10/1975 | Payne | 209/74 |
| 3,980,180 | 9/1976 | Jamieson | 209/565 |
| 4,091,931 | 5/1978 | Button | 209/73 |
| 4,671,652 | 6/1987 | van Asselt et al. | 356/66 |
| 4,901,861 | 2/1990 | Cicchelli | 209/539 |
| 4,903,635 | 2/1990 | Hebrank | 119/1 |
| 5,017,003 | 5/1991 | Keromnes et al. | 356/53 |
| 5,699,751 | 12/1997 | Phelps et al. | 119/6.8 |
| 5,713,473 | 2/1998 | Satake et al. | 209/580 |
| 5,745,228 | 4/1998 | Hebrank et al. | 356/53 |

*Primary Examiner*—Donald P. Walsh
*Assistant Examiner*—Jonathan R Miller
*Attorney, Agent, or Firm*—Myers Bigel Sibley & Sajovec, P.A.

[57] ABSTRACT

Methods and apparatus are provided for removing clear avian eggs from a moving egg flat without contacting the removed eggs and without contaminating the eggs remaining within the egg flat. Clear eggs are identified by passing an egg flat between respective pairs of light sources and light detectors and detecting the amount of light that passes through each egg. Clear eggs are then ejected from the moving egg flat into a stationary receptacle located above the moving egg flat by applying a first stream of air to the lower end of the clear egg. A second stream of air may also be applied to the egg after the egg has been lifted from the egg flat by the first stream of air. This second stream of air is applied to the egg along a direction substantially transverse to the first stream of air. A third stream of air may be utilized to dislodge an egg from a stuck condition prior to being ejected from the egg flat.

78 Claims, 14 Drawing Sheets

METHODS AND APPARATUS FOR REMOVING EGGS FROM A MOVING EGG FLAT

FIELD OF THE INVENTION

The present invention relates generally to eggs and, more particularly, to methods and apparatus for handling eggs.

BACKGROUND OF THE INVENTION

Advances in poultry embryology have made possible the addition of various materials to the embryo or to the environment around the embryo within an avian egg for the purpose of encouraging beneficial effects in the subsequently hatched chick. Such beneficial effects include increased growth, prevention of disease, increasing the percentage hatch of multiple incubated eggs, and otherwise improving physical characteristics of hatched poultry. Additionally, certain types of vaccinations which could previously only be carried out upon either recently hatched or fully mature poultry can now be successful in the embryonated chick.

In ovo vaccination techniques can increase vaccination efficiency and can reduce stress on young chicks caused by injection. Conventional in ovo inoculating devices typically inject all eggs contained within an egg flat. An exemplary in ovo inoculating device that injects all eggs contained within an egg flat is described in U.S. Pat. No. 4,903,635 to Hebrank.

Unfortunately, it may not be desirable to administer vaccinations into every egg contained within an egg flat. For example, "clear" eggs are eggs that do not contain an embryo and, thus, may not subsequently hatch as a chick. The administration of vaccinations into clear eggs generally serves no purpose and may be considered wasteful. In addition, mold may grow in clear eggs that have been injected, thus increasing the risk of exposing other eggs and hatched chicks to undesirable contamination. Furthermore, injected clear eggs may increase the risk of contamination resulting from albumin leaking therefrom. Accordingly, it would be desirable to quickly identify and remove clear eggs from an egg flat prior to the in ovo administration of vaccinations via automatic inoculating devices.

SUMMARY OF THE INVENTION

It is, therefore, an object of the present invention to facilitate the removal of clear eggs from an egg flat prior to the in ovo administration of vaccinations via an inoculating device.

It is another object of the present invention to facilitate the removal of eggs from an egg flat wherein the risk of contamination from contact with the removed egg or breakage of the removed egg is reduced.

It is another object of the present invention to facilitate cost savings associated with in ovo administration of vaccinations.

These and other objects of the present invention are provided by methods and apparatus for removing avian eggs, and particularly clear avian eggs, from a moving egg flat prior to inoculation without contacting the removed egg and without contaminating the eggs remaining within the egg flat. According to the present invention, clear eggs are identified by passing an egg flat between respective pairs of light sources and light detectors and detecting the amount of light that passes through each egg. Clear eggs are then ejected from the moving egg flat into a stationary receptacle located above the moving egg flat by applying a first stream of air to a lower end of each clear egg. A second stream of air may also be applied to each egg after the egg has been lifted from the egg flat by the first stream of air. This second stream of air is applied to an egg along a direction substantially transverse to the first stream of air.

According to another embodiment of the present invention, a duct may be utilized to direct clear eggs from an egg flat to a receptacle. A separate duct may be utilized for each egg within a row of an egg flat. In addition, a vacuum may be applied to a duct so as to pull an egg upwardly and through the duct.

According to another embodiment of the present invention, a single stream of air may be utilized to eject a clear egg into a receptacle located directly over the clear egg. Alternatively, a a single stream of air may be utilized to direct a clear egg towards an angled member positioned above the moving egg flat such that the ejected egg bounces off the angled member and into an overhead receptacle.

The methods and apparatus for ejecting eggs from an egg flat according to the present invention are advantageous because eggs can be removed quickly and with little risk of contamination. Because only air touches the removed egg, there are no additional components that require cleaning and/or sterilization. Furthermore, the risk of contamination during removal, caused by egg breakage, may be reduced because eggs can be removed intact. The present invention may be economically advantageous because eggs not containing an embryo can be removed prior to receiving a vaccination injection, thus resulting in vaccine savings.

According to another embodiment of the present invention, eggs carried by an egg flat may be released from a stuck condition by limiting vertical movement of the eggs and then applying a stream of air to the lower end thereof. This aspect of the present invention is particularly advantageous because eggs in a stuck condition may break and/or fail to reach the receptacle when ejected, thus increasing the risk of contaminating the remaining eggs within an egg flat as well as the inoculating device.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1A:
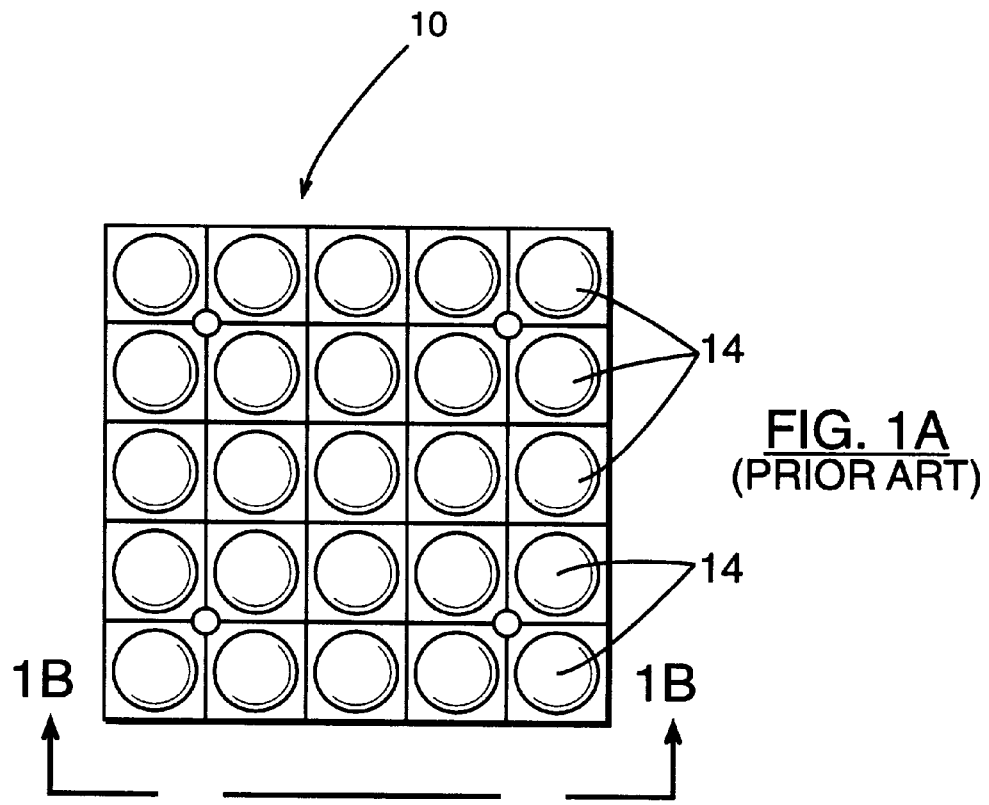
FIG. 1A is a top plan view of an egg flat configured to carry twenty-five eggs in an array of five rows of five eggs each, wherein each egg is supported in a substantially vertical position.
Figure 1B:
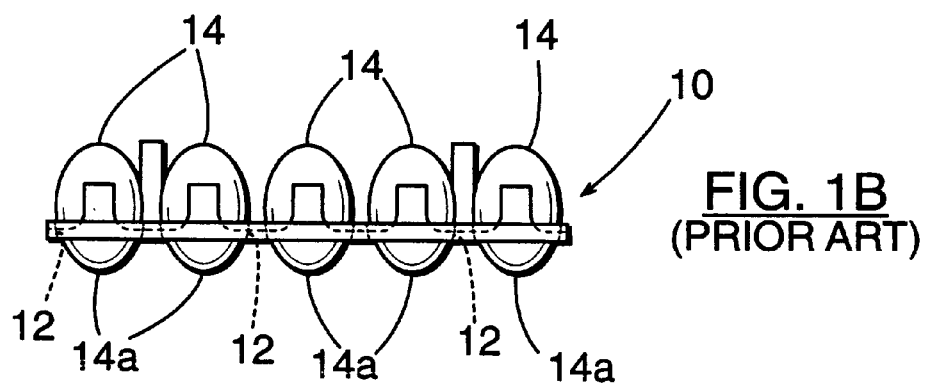
FIG. 1B is a side elevation view of the flat of FIG. 1A.

The methods and apparatus of the present invention may be carried out with any type of avian eggs, including chicken, turkey, duck, geese, quail, and pheasant eggs. Chicken eggs are particularly preferred. The methods and apparatus of the present invention are particularly adapted for use with egg carriers often referred to as "flats." An exemplary egg flat 10 is illustrated in FIGS. 1A and 1B. The illustrated egg flat 10 includes a plurality of rows of apertures 12. Each aperture 12 is configured to receive a first or large end 14a of a respective egg 14 so as to support the respective egg 14 in a substantially vertical position (FIG. 1B).

The illustrated egg flat 10 carries twenty-five eggs in an array of five rows of five eggs each. However, an egg flat used in accordance with the present invention may contain any number of rows containing any number of eggs. Furthermore, eggs in adjacent rows may be parallel to one another, as in a "rectangular" flat, or may be in a staggered relationship, as in an "offset" flat. Examples of commercial egg flats with which the present invention may be used include, but are not limited to, the "CHICKMASTER 54" flat, the "JAMESWAY 42" flat, and the "JAMESWAY 84" flat (in each case, the number indicates the number of eggs carried by the egg flat).

Figure 2:
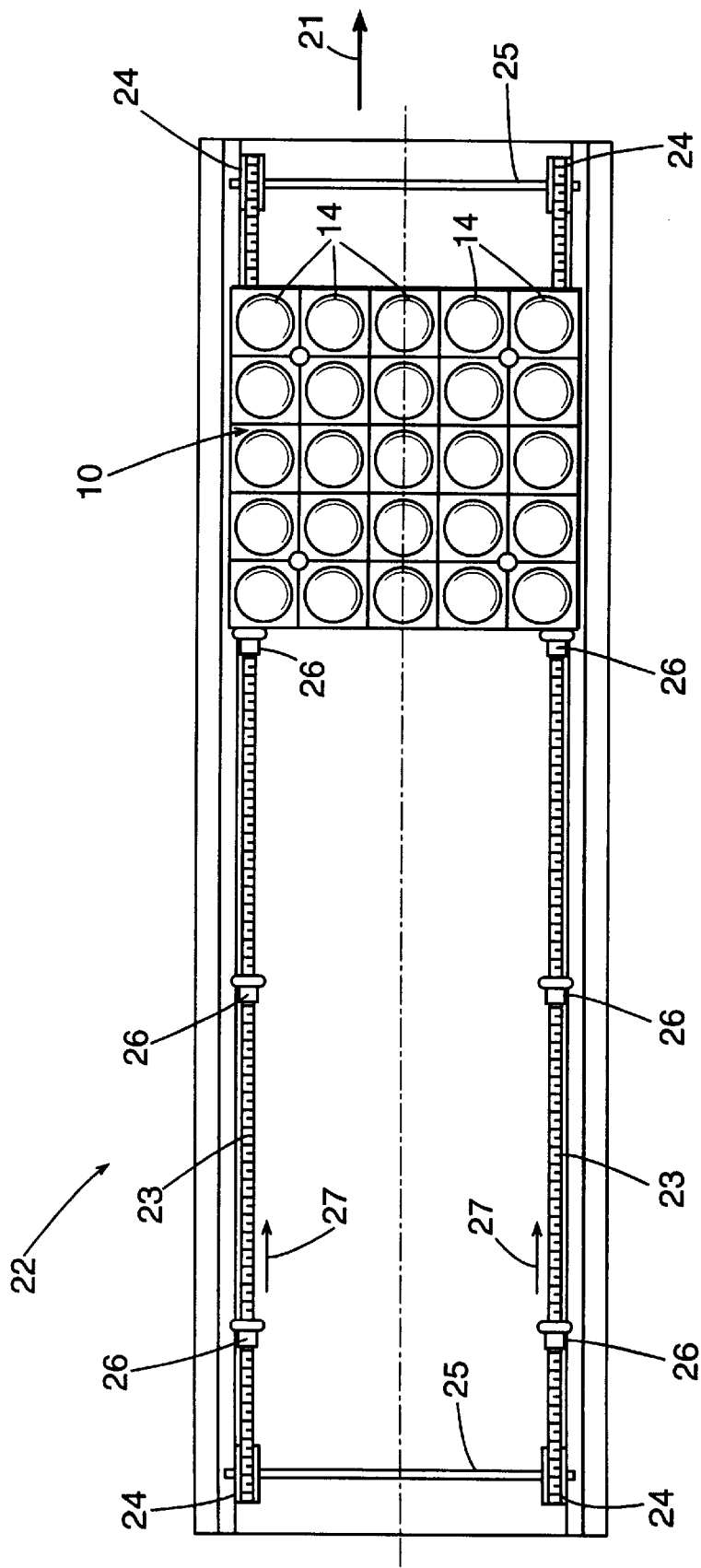
FIG. 2 is a plan view of the egg flat of FIGS. 1A–1B being transported along a horizontal direction via a conveyor system that is part of an in ovo inoculation device.

Referring now to FIG. 2, an exemplary egg flat conveyor system 22 for moving egg flats 10 along a horizontal direction (indicated by arrow 21) in conjunction with an inoculation device is illustrated. Egg flats with which the present invention may be utilized are typically moved via conveyor systems at rates of between about 0.4 feet per second and about 1.5 feet per second. The illustrated conveyor system 22 includes a pair of endless belts 23. Each of the belts 23 is driven in the direction indicated by arrows 27 via a respective pair of drive sprockets 24 and shafts 25. A plurality of pairs of dogs 26 connected to the endless belts 23 move respective egg flats 10 along the horizontal direction 21.

Conveyor systems for moving flats of eggs are well known by those skilled in this art and need not be described further herein. It is understood that other egg flat conveyor systems may be utilized in carrying out the present invention. Accordingly, the present invention is not limited to the conveyor system 22 illustrated in FIG. 2. Exemplary egg flat conveyor systems for use with the present invention are disclosed in U.S. Pat. No. 5,745,228 to Hebrank et al., and U.S. Pat. No. 4,903,635 to Hebrank, the disclosures of which are incorporated herein by reference in their entireties.

Figure 3:
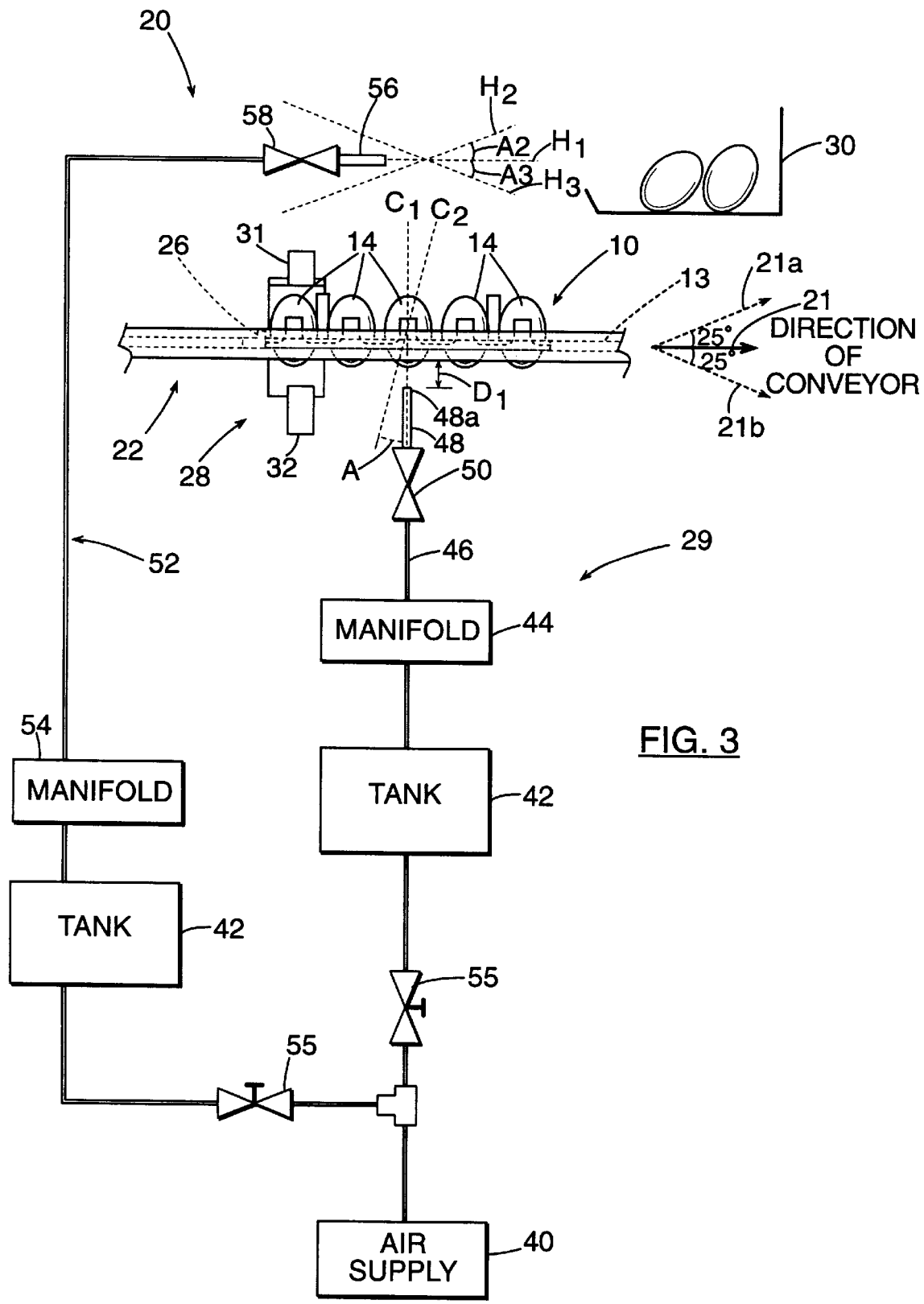
FIG. 3 is a side elevation view of an apparatus according to an embodiment of the present invention for ejecting eggs from a moving egg flat into a stationary, overhead receptacle.

Referring now to FIG. 3, an apparatus 20 for removing eggs from a moving egg flat 10 according to an embodiment of the present invention is illustrated. The illustrated apparatus 20 includes an egg flat conveyor system 22, a clear egg identification system 28, and a clear egg ejection system 29 for ejecting identified clear eggs from the egg flat 10 into a stationary receptacle 30 located above the moving egg flat 10.

The clear egg identification system 28 includes a plurality of light sources 31 positioned on one side of the egg flat 10 and a corresponding plurality of light detectors 32 positioned on the other side of the egg flat 10 opposite the light sources 31, as illustrated. The light detectors 32 are configured to identify clear eggs based upon an amount of light from a respective light source 31 that passes through an egg 14. An exemplary clear egg identification system is disclosed in U.S. Pat. No. 5,745,228 to Hebrank et al.

It is understood that the positions of the illustrated light sources 31 and light detectors 32 are not critical and could be reversed. In addition, a light source 31 and light detector 32 could be placed in different orientations, so long as light from a light source 31 can pass through an egg 14 to a light detector 32.

In addition, other devices for detecting clear eggs, as well as eggs with other characteristics, can be utilized with the present invention. For example, U.S. Pat. Nos. 4,955,728 and 4,914,672, both to Hebrank, describe a candling apparatus that uses infrared detectors and the infrared radiation emitted from an egg to distinguish live from infertile eggs. U.S. Pat. No. 4,671,652 to van Asselt et al. describes a candling apparatus in which a plurality of light sources and corresponding light detectors are mounted in an array, and the eggs passed on a flat between the light sources and the light detectors.

The egg flat conveyor system 22 is configured to transport the illustrated egg flat 10 between the light sources 31 and light detectors 32 in a substantially horizontal direction such that each egg 14 within a row of the egg flat 10 is positioned between a light source 31 and a corresponding light detector 32. The term "substantially horizontal", is intended to include angles of up to about twenty-five degrees (25°) relative to horizontal. As illustrated in FIG. 3, direction 21 is intended to represent a horizontal direction, and directions 21a and 21b are intended to represent directions of up to about twenty-five degrees (25°) relative to horizontal. However, it is understood that the present invention is not limited to the illustrated embodiment. The present invention may be utilized with egg flat conveyor systems that move egg flats in various directions relative to horizontal.

The illustrated clear egg ejection system 29 includes a source or supply of pressurized air 40, a tank 42 which serves as means for maintaining substantially constant air pressure, a manifold 44, and a first set of air lines 46 extending from the manifold 44 (FIG. 4A) that are in fluid communication with the pressurized air supply 40. Each of the air lines 46 in the first set includes a nozzle 48 that is positioned adjacent a first end 14a of a respective egg 14 within a respective row of an egg flat 10 passing thereover. Preferably, each nozzle 48 is positioned between about one-quarter inch (0.25") and about one and one-quarter inch (1.25") from a first end 14a of a respective egg 14 and indicated as D in FIG. 3.

Figure 4:
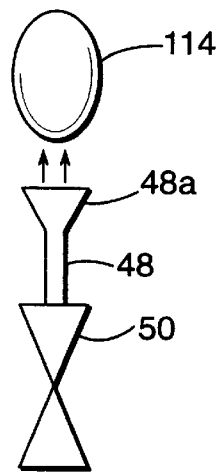
FIG. 4 illustrates a nozzle for use in ejecting an egg from an egg flat according to the present invention wherein the nozzle has a diverging end portion.
Figure 5A:
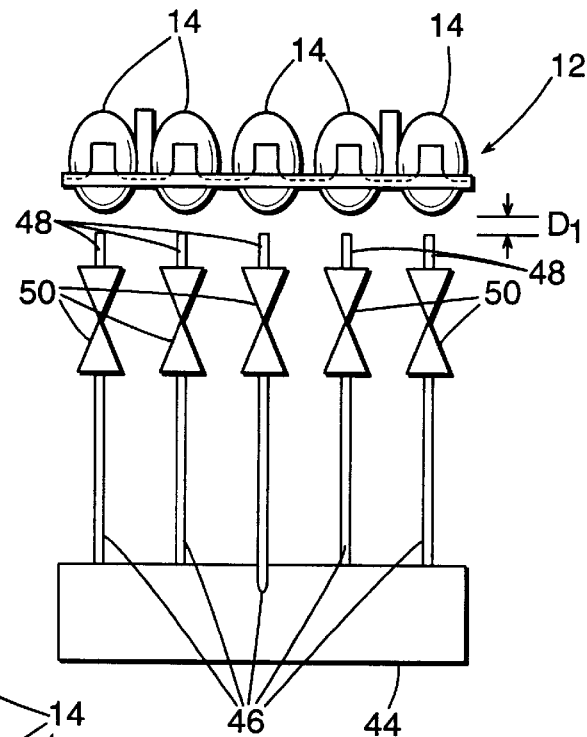
FIG. 5A is a side elevation view of a first set of air lines used by the apparatus of FIG. 3, wherein each air line includes a nozzle that is positioned adjacent the first end of a respective egg within a respective row of an egg flat passing thereover.
Figure 5B:
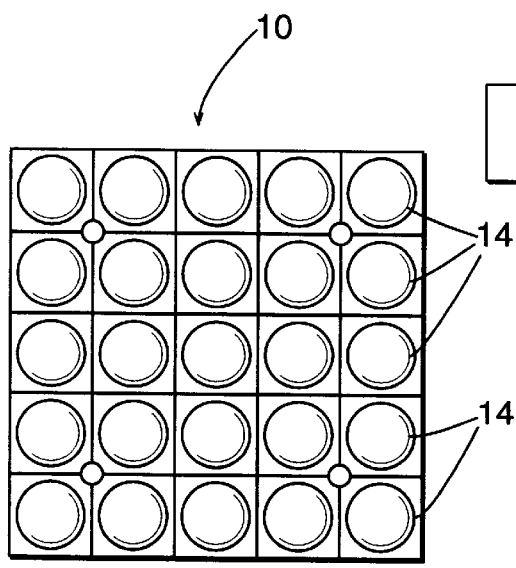
FIG. 5B is a top plan view of an egg flat passing through the apparatus of FIG. 3 illustrating a second set of air lines, wherein each air line includes a nozzle that is positioned above the moving egg flat and adjacent the trajectory path of a respective egg from the egg flat to a receptacle FIG. 6 schematically illustrates operations for carrying out various aspects of the present invention.
Figure 5B:
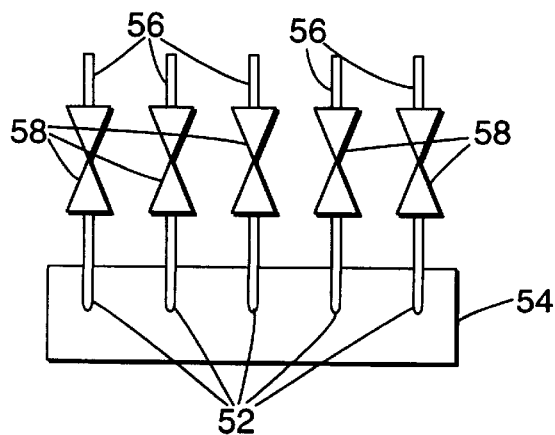

According to a preferred embodiment of the present invention, each air line 46 in the first set is formed from tubing (e.g., stainless steel tubing, or copper tubing) having an inner diameter of between about 0.1875 inches and about 0.5 inches. Each nozzle 48 is preferably a one-eighth inch (⅛") NPT (National Pipe Thread)fitting (Eldon James, Loveland, Colo.). In the illustrated embodiment of FIG. 3, each nozzle 48 has an end portion 48a with a generally straight configuration. However, as illustrated in FIG. 4, a nozzle 48 may also have an end portion 48a with a diverging configuration.

The tank 42 preferably has a volume of between about five (5) gallons and about twenty (20) gallons to ensure that pressure is maintained substantially constant during the period of time that air is applied to an egg to eject the egg into the receptacle.

As illustrated in FIG. 3, each nozzle 48 may be oriented along a vertical direction (indicated by C1). Alternatively, each nozzle 48 may be oriented adjacent an egg first end 14a at an angle relative to vertical. For example, as illustrated in FIG. 3, each nozzle 48 may be oriented along a non-vertical direction (indicated by C2) and may have an angle A relative to vertical of between about zero degrees and about ten degrees (0°–10°).

Each air line 46 in the first set also preferably includes a valve 50 located between a respective nozzle 48 and the manifold 44. Each valve 50 serves as means for controlling a first stream of air from the pressurized air supply 40 through the nozzle 48 for a predetermined period of time. A particularly preferred valve 50 for controlling a stream of air from the pressurized air supply 40 through the nozzle 48 is a 0.5 inch poppet valve manufactured by Spartan Scientific, Youngstown, Ohio. However, it is understood that the present invention is not limited to the use of poppet valves. Various types of valves may be utilized in carrying out the present invention.

The clear egg ejection system 26 may also include a second set of air lines 52 extending from a manifold 54 and in fluid communication with the pressurized air supply 40. As illustrated in FIG. 4B, each of the second set of air lines 52 may include a respective nozzle 56 positioned above the moving egg flat 10 and adjacent the trajectory path of a respective egg 14 from the egg flat 10 to the receptacle 30.

As illustrated in FIG. 3, each nozzle 56 may be oriented along a generally horizontal direction as indicated by H1. Each nozzle 56 may also be oriented along a direction H2 which has an angle A2 relative to horizontal of between about zero degrees and about forty-five degrees (0°–45°). Each nozzle 56 may also be oriented along a direction H3 which has an angle A3 relative to horizontal of between about zero degrees and about forty-five degrees (0°–45°).

Figure 7:
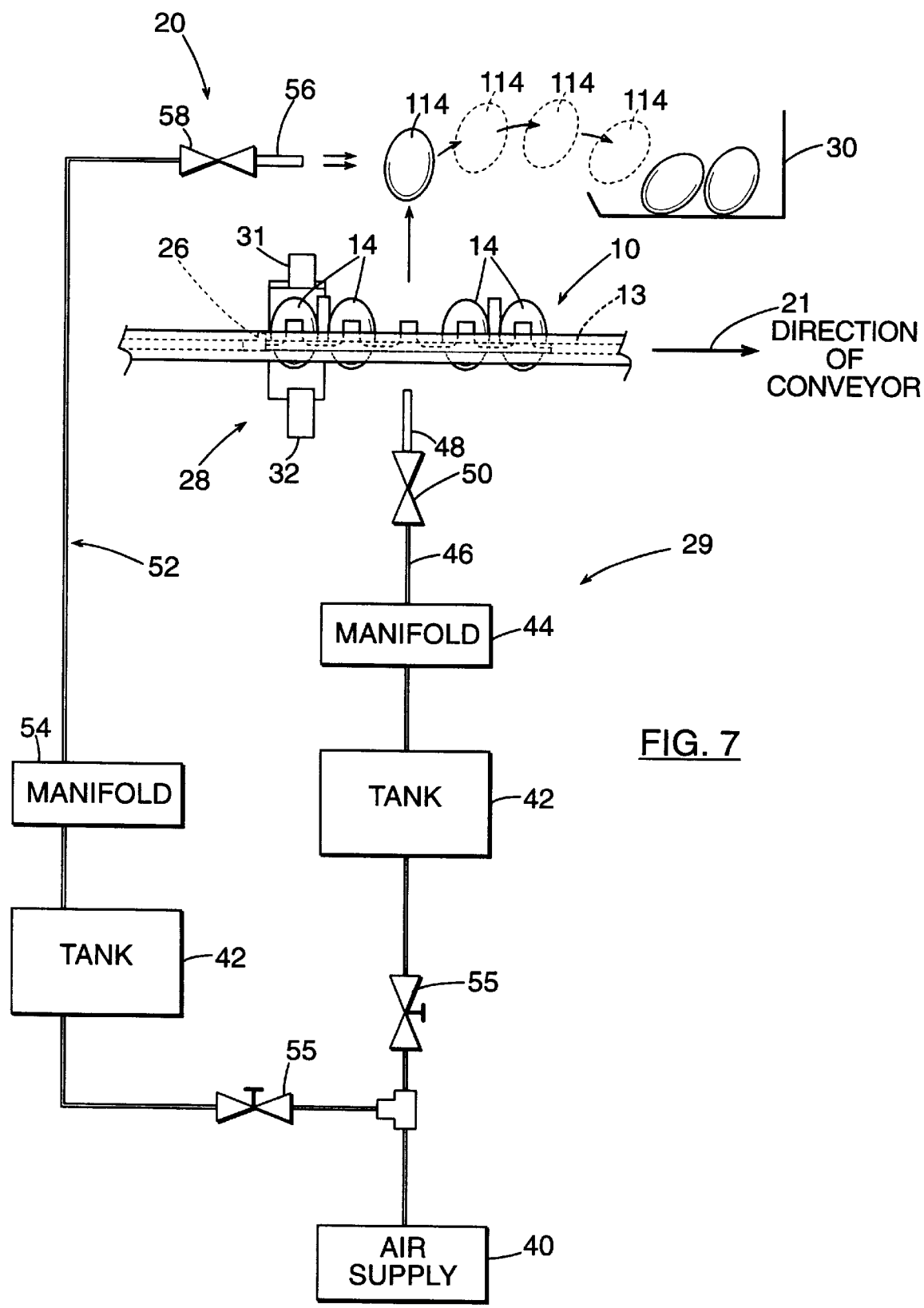
FIG. 7 is a side elevation view of the apparatus of FIG. 3 illustrating a clear egg being ejected from the moving egg flat into a stationary receptacle positioned above the egg flat via a first stream of air applied to the lower end of the egg and a second stream of air applied to the egg along a direction substantially transverse to the first stream of air.

Each air line 52 in the second set also includes a valve 58 located between the nozzle 56 and manifold 54. Each valve 58 serves as means for providing a second stream of air from the pressurized air supply 40 through a respective nozzle 56 for a predetermined period of time after the first stream of air has been applied to an ejected egg first end 14a. The second stream of air is applied to an ejected egg along a direction substantially transverse to the first stream of air, as illustrated in FIG. 7. A particularly preferred valve for providing a stream of air from the pressurized air supply 40 through the nozzle 56 is a two-way spool valve manufactured by Humphrey, Kalamazoo, Mich. However, the present invention is not limited to the use of spool valves. Accordingly, various types of valves may be utilized.

In the illustrated embodiment of FIG. 3, pressure regulation valves 55 are provided to regulate pressure within the first and second sets of air lines 46, 52 as would be understood by those skilled in this art. Various types of valves could be used to regulate pressure within the first and second sets of air lines 46, 52 and need not be described further herein.

In addition, it is understood that the present invention is not limited to the illustrated arrangement of the first and second sets of air lines 46, 52. Various configurations and arrangements, with and without valves, may be utilized without departing from the spirit and intent of the present invention.

Figure 6:
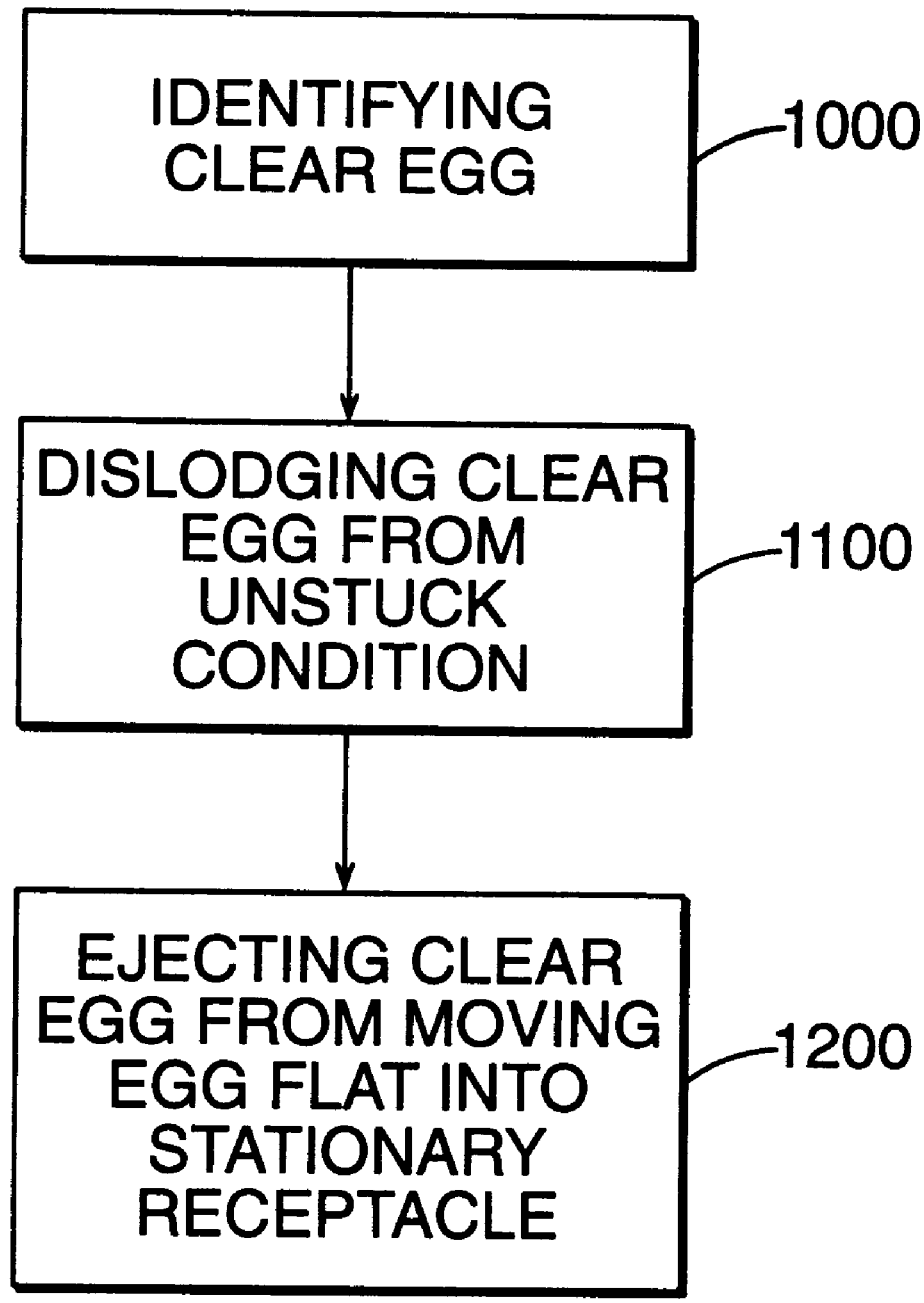

Referring now to FIG. 6, operations for removing avian eggs from an egg flat according to the present invention are schematically illustrated. Initially, one or more eggs within a row of an egg flat are identified as being clear eggs (Block 1000). Preferably, clear egg identification is performed by detecting an amount of light that passes through an egg. It is understood that other identifiable characteristics of an egg could qualify an egg for removal via the present invention, including, but not limited to, a dead egg, a diseased egg and a broken egg. The present invention is not limited to the removal of clear eggs.

Still referring to FIG. 6, each identified clear egg is then dislodged slightly from the egg flat to ensure that the egg has not become stuck within the egg flat (Block 1100). The step of dislodging a clear egg in a stuck condition may be performed by limiting vertical movement of the stuck egg and then applying a stream of air to the lower end of the clear egg.

Next, the clear egg is ejected from the egg flat into a stationary receptacle located above the moving egg flat (Block 1200). Alternatively, clear eggs could be ejected onto a conveyor system that is configured to transport the ejected eggs to a disposal receptacle. The step of ejecting an egg from an egg flat may be performed by applying a first stream of air to the lower end of the clear egg. Alternatively, a second stream of air may be applied to the egg along a direction substantially transverse to the first stream of air after the first stream of air has been applied.

Referring now to FIG. 7, operations for ejecting eggs via the apparatus 20 of FIG. 3 are illustrated. An egg 114 within the third row of the moving egg flat 10 has been identified as being a clear egg via the clear egg identification system 28 (Block 1000, FIG. 6). As the clear egg 114 passes over a nozzle 48 of a respective air line 46 of the first set, the clear egg 114 is ejected upwardly by a first stream of air having a pressure between about thirty pounds per square inch and about one hundred twenty pounds per square inch (30 psi–120 psi) applied to the first end 114a of the clear egg 114 for a duration of between about 30 milliseconds and about 100 milliseconds.

A second stream of air is then applied to the ejected clear egg 114 via a nozzle 56 of a respective air line 52 of the second set after the first stream of air has been applied. The second stream of air having a pressure of between about thirty pounds per square inch and about one hundred twenty pounds per square inch (30 psi–120 psi) is applied to the selected egg 114 along a direction substantially transverse to the first stream of air for a duration of between about 30 milliseconds and about 100 milliseconds. As illustrated, the momentum of the ejected clear egg 114 in the direction 21, in combination with the force of the first and second streams of air, directs the clear egg 114 into the stationary receptacle 30 (Block 1200, FIG. 6).

In addition, eggs can be ejected according to the present invention in various directions. For example, an egg can be ejected upwardly and sideways (i.e., 90° to the direction of travel of the egg flat 10). Furthermore, a sterilized fluid stream, such as sterilized water, may be utilized to eject an egg from a moving egg flat in accordance with the present invention in lieu of air.

Preferably, the illustrated receptacle 30 is configured such that an egg can be ejected therewithin without breaking. Furthermore, it is preferred that the receptacle 30 is configured to prevent contamination from ejected eggs contained therewithin from falling back down upon egg flats 10 passing therebeneath. As would be understood by those skilled in this art, the stationary receptacle 30 may include a conveyor system for transporting ejected eggs received therein to a disposal area.

In the illustrated embodiment of FIG. 7, the ejected clear egg 114 is located two rows downstream from the row of eggs 14 currently being analyzed via the clear egg identification system 28. It is to be understood, however, that eggs can be ejected from an egg flat according to the present invention at any time and from any row after being analyzed via the clear egg identification system 28. In addition, any number of eggs within a row can be ejected at the same time, according to the present invention.

Figure 8:
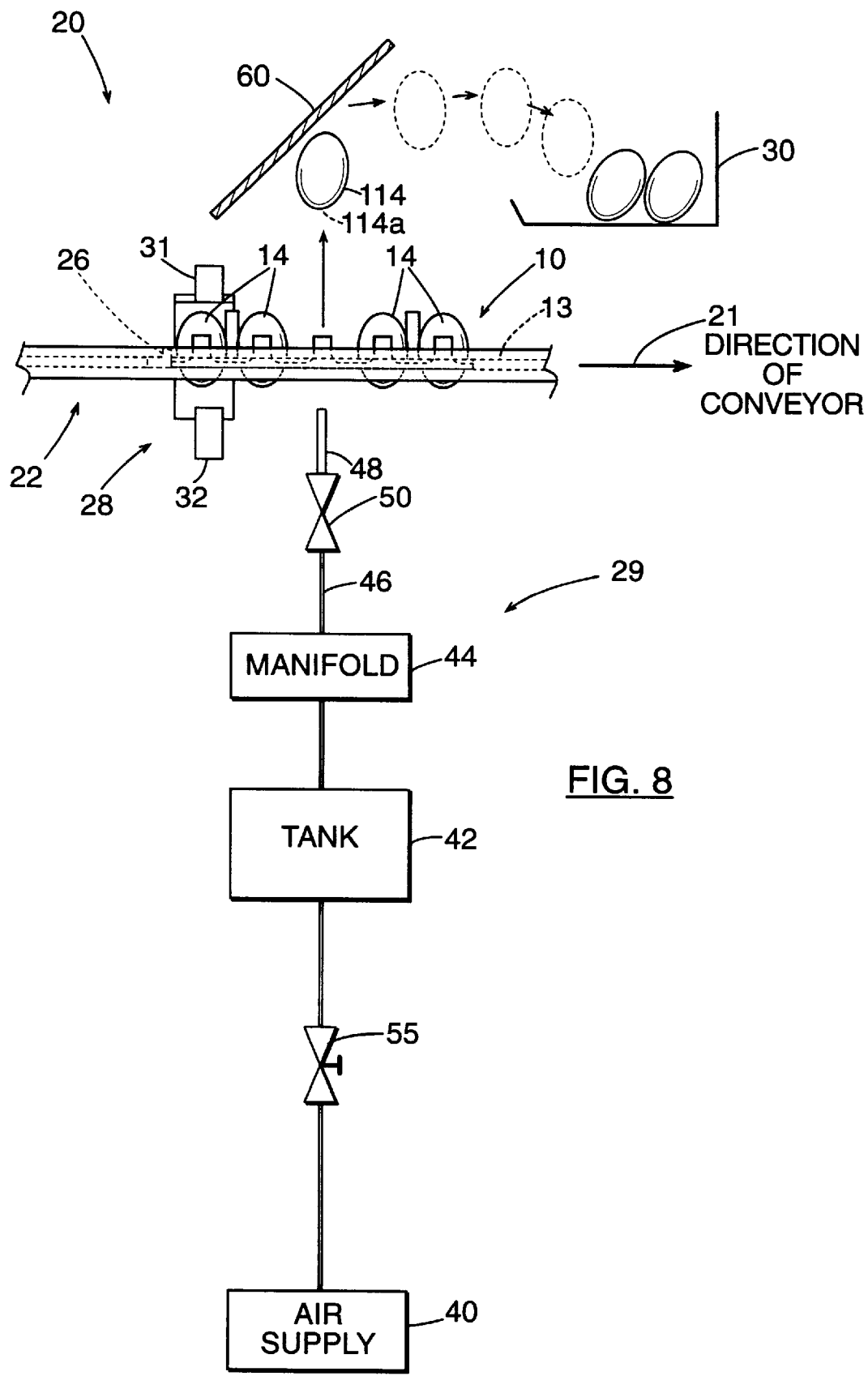
FIG. 8 is a side elevation view of an apparatus according to another embodiment of the present invention wherein an egg is being ejected from a moving egg flat into a stationary receptacle positioned above the egg flat via a stream of air applied to the lower end of the egg such that the egg bounces off an angled member and into the receptacle.

Referring now to FIG. 8, another embodiment of the present invention is illustrated. In this embodiment, a single stream of air is applied to the first end 114a of a clear egg 114 to be ejected. The clear egg 114 bounces off of an angled member 60 positioned above the moving egg flat 10 and into the receptacle 30. Preferably, the member 60 is formed from a material and/or has a configuration that does not cause the clear egg 114 to break when contact is made with the angled (or curved) member 60.

Figure 9:
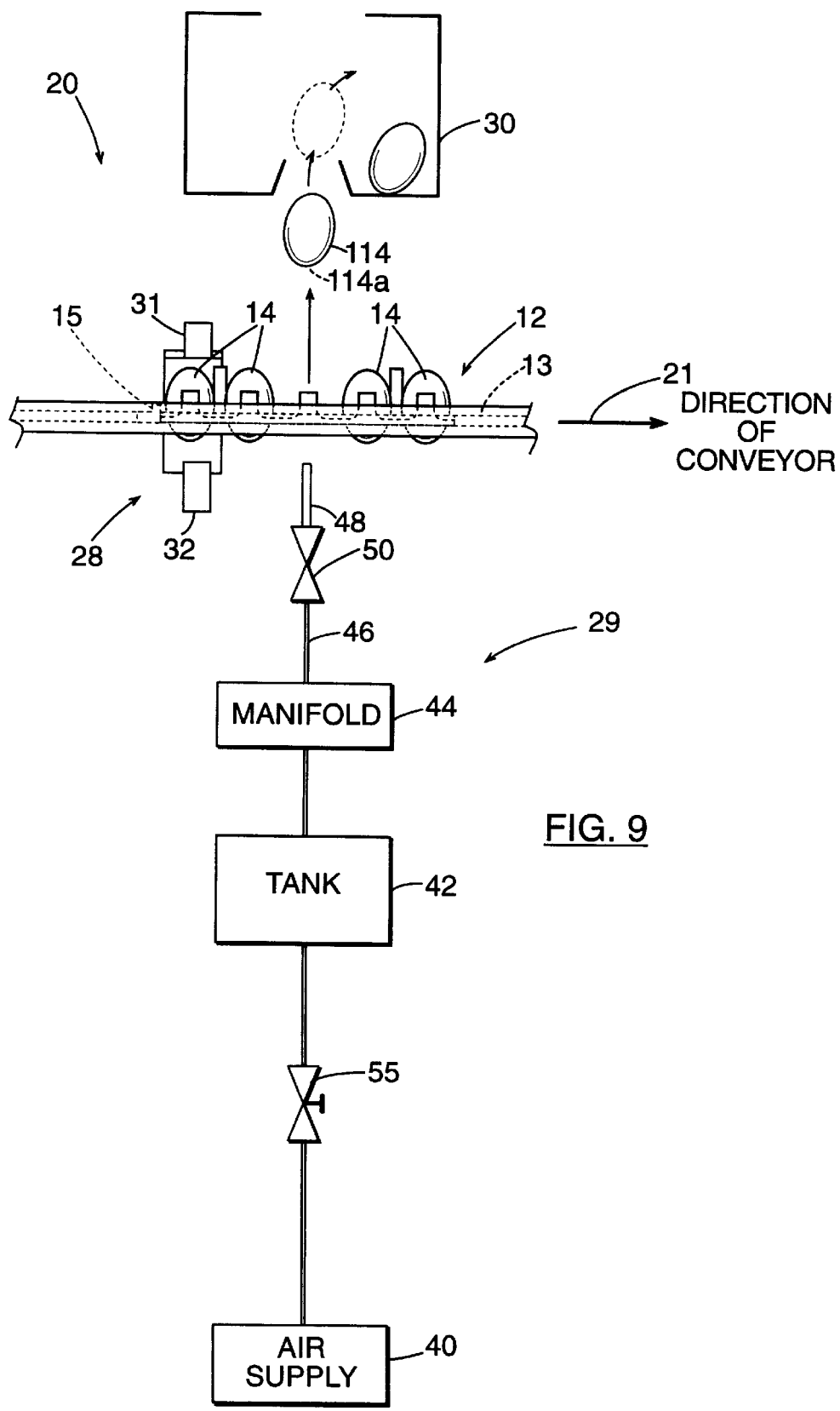
FIG. 9 is a side elevation view of an apparatus according to another embodiment of the present invention wherein an egg is being ejected from a moving egg flat into a stationary receptacle positioned directly above the egg via a stream of air applied to the lower end of the egg.

Referring now to FIG. 9, another embodiment of the present invention is illustrated. In this embodiment, a single stream of air is applied to the first end 114a of a clear egg 114 to be ejected. The single stream of air directs the clear egg 114 upwardly into a receptacle 30 that is positioned above the clear egg 114. Preferably, the illustrated receptacle 30 of FIG. 7 is configured such that an egg can be ejected therewithin without breaking. Furthermore, it is preferred that the receptacle 30 of FIG. 8 is configured to prevent contamination from ejected eggs contained therewithin from falling back down upon egg flats 10 passing therebeneath.

Figure 10A:
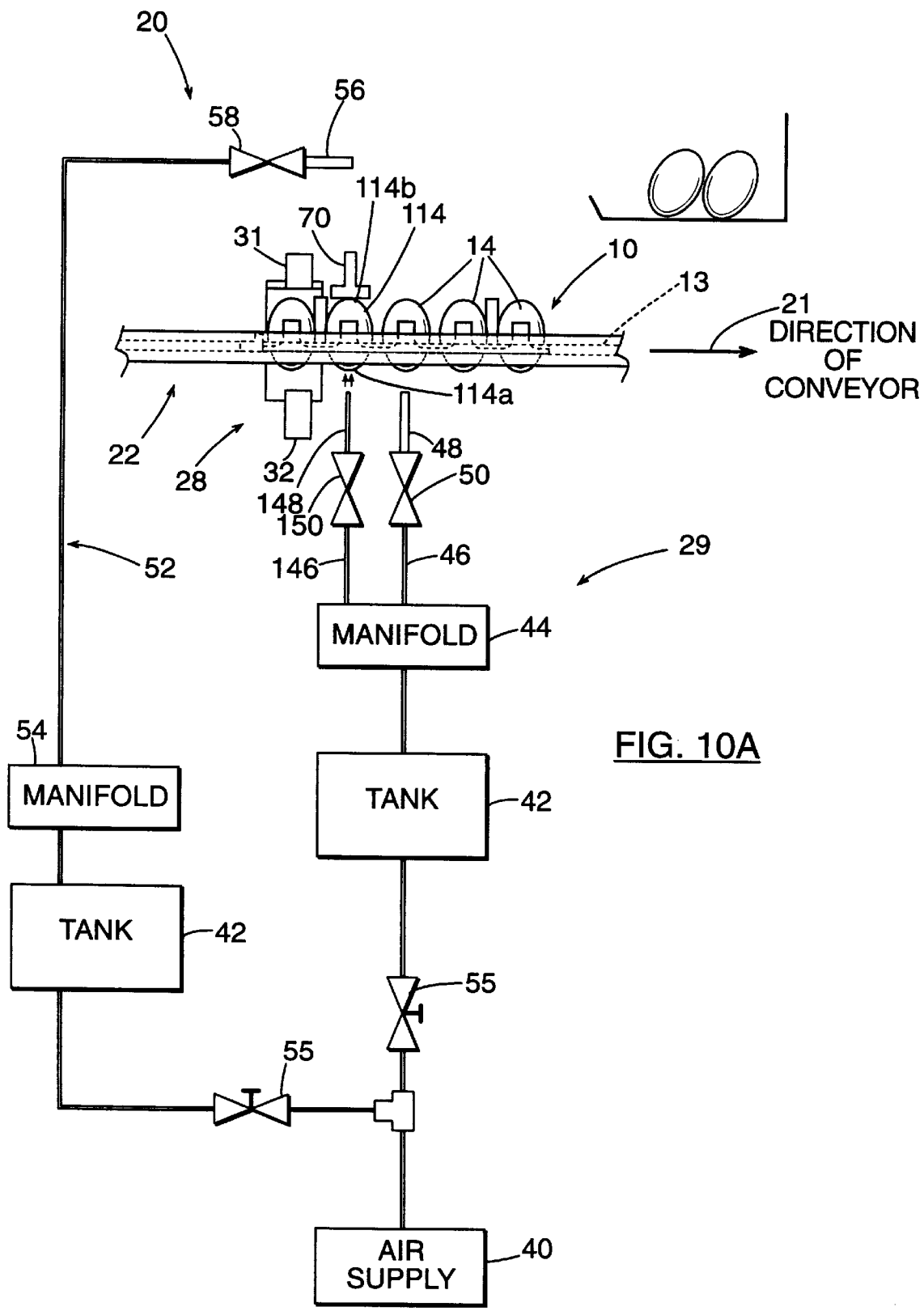
FIG. 10A is a side elevation view of an apparatus according to another embodiment of the present invention wherein an egg is being dislodged from a stuck condition within the egg flat via a stream of air applied to the lower end of the egg, and wherein vertical movement of the egg is limited.
Figure 10B:
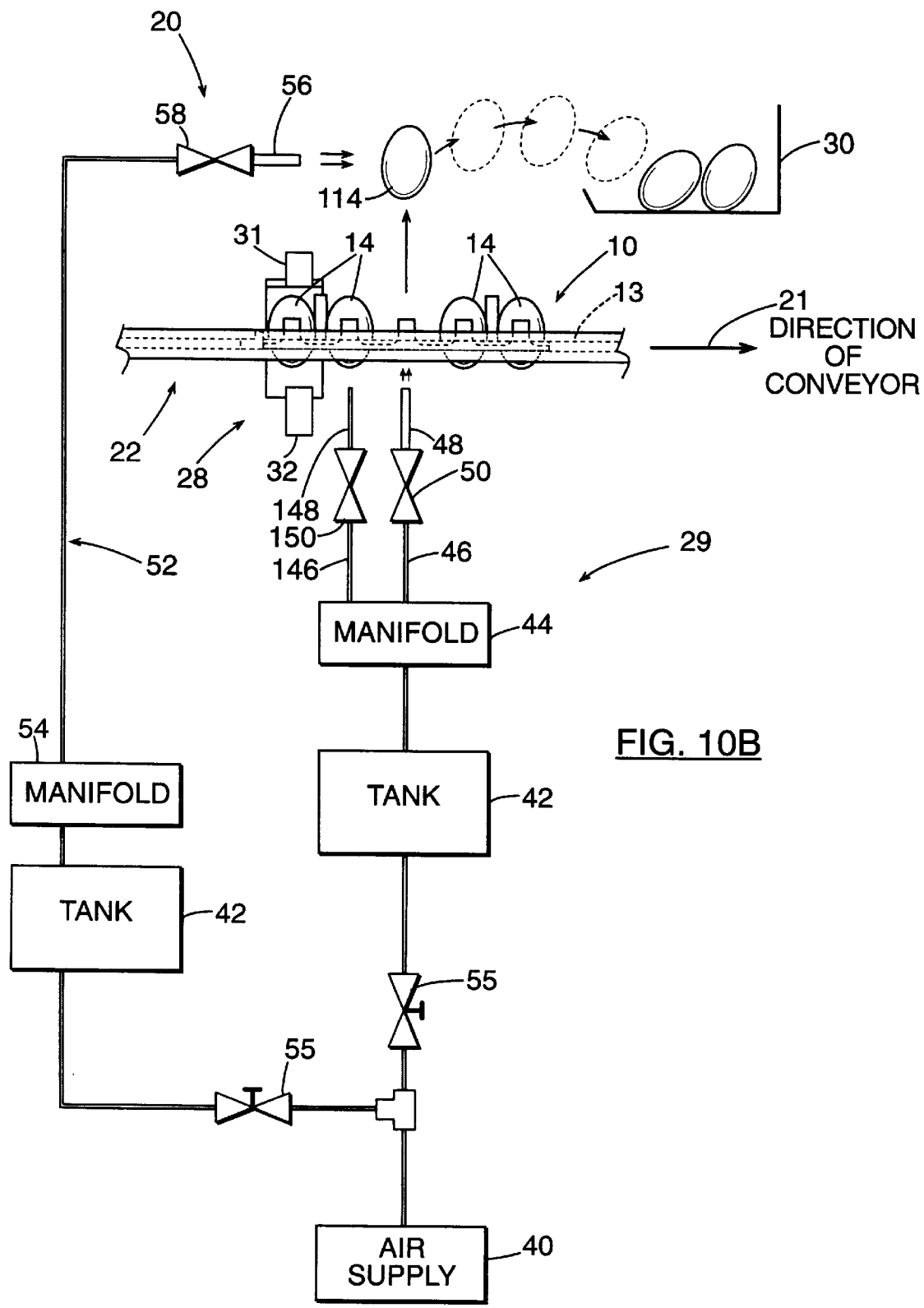
FIG. 10B is a side elevation view of the apparatus of FIG. 10A wherein the egg previously dislodged from a stuck condition is ejected into a stationary receptacle positioned above the egg flat.

Referring now to FIGS. 10A and 10B, another embodiment of the present invention is illustrated. In this embodiment, a stream of air may be utilized as means for dislodging an egg 14 from a stuck condition within an egg flat 10 (Block 1100, FIG. 6). This embodiment of the present invention may be utilized both for eggs to be injected in ovo and for eggs to be removed from the egg flat 10. In FIG. 10A, an egg 114, identified as being clear via the clear egg identification system 28, is restrained from vertical movement that would tend to dislodge the egg 114 from the egg flat 10 via a restraining member 70 placed at a second end 114b of the egg opposite the first end 114a. A stream of air is then applied to the first end 114a of the clear egg 114 for a predetermined period of time to dislodge the clear egg 114 from a stuck condition. The restraining member 70 applies a force to the egg in a direction counter to the stream of air to limit vertical movement of the egg. Alternatively, another stream of air could be applied to the egg in a direction counter to the stream of air that is used to dislodge the egg from a stuck condition in order to limit vertical movement of the egg.

The stream of air may be provided via an air line 146 from a third set of air lines in fluid communication with the pressurized air supply 40 via the manifold 44, as illustrated. Each air line 146 in the third set is preferably aligned with a respective egg 14 in each row of an overlying egg flat 10. Accordingly, each egg 14 in a row can be dislodged from a stuck condition, if necessary.

In the illustrated embodiment, each air line 146 in the third set includes a valve 150 located between a nozzle 148 and the manifold 44 that serves as means for providing a stream of air from the pressurized air supply 40 through the nozzle 148 for a predetermined period of time.

In the illustrative embodiment, once the clear egg 114 is dislodged from a stuck condition, the egg flat 10 moves in the direction 21 such that the clear egg 114 is positioned above the first nozzle 48. The clear egg 114 is then ejected as described above and as illustrated in FIG. 10B.

Alternatively, the step of dislodging an egg from a stuck condition could be performed by an air line 46 in the first set of air lines prior to the step of ejecting an egg from the egg flat 10. Furthermore, the step of dislodging an egg from a stuck condition could be performed by applying a stream of fluid, including, but not limited to, water to an egg in accordance with the present invention.

Figure 11:
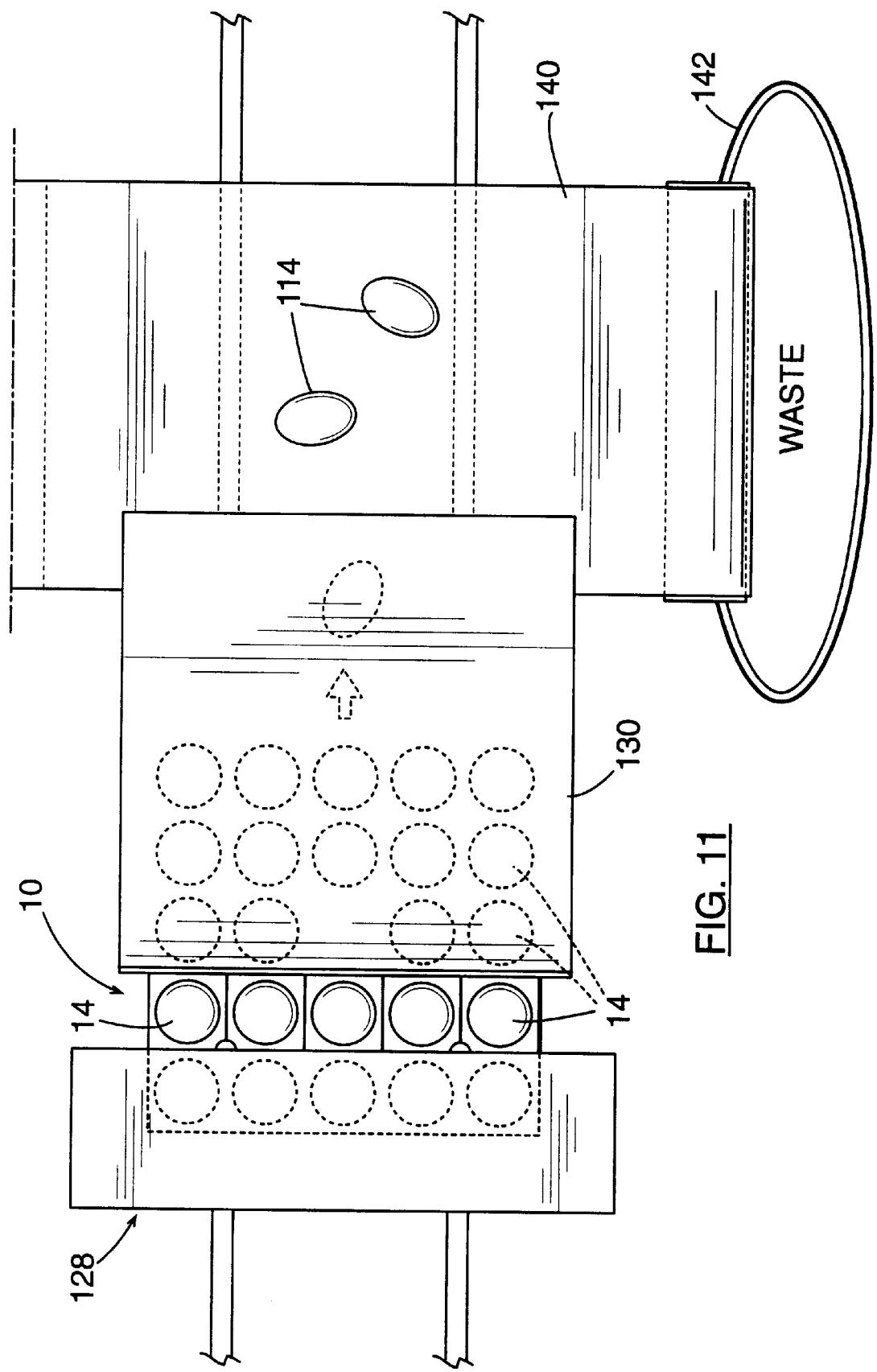
FIG. 11 is a top plan view of an egg flat passing through an apparatus according to an embodiment of the present invention wherein a duct is utilized to direct ejected eggs onto a conveyor system.
Figure 12:
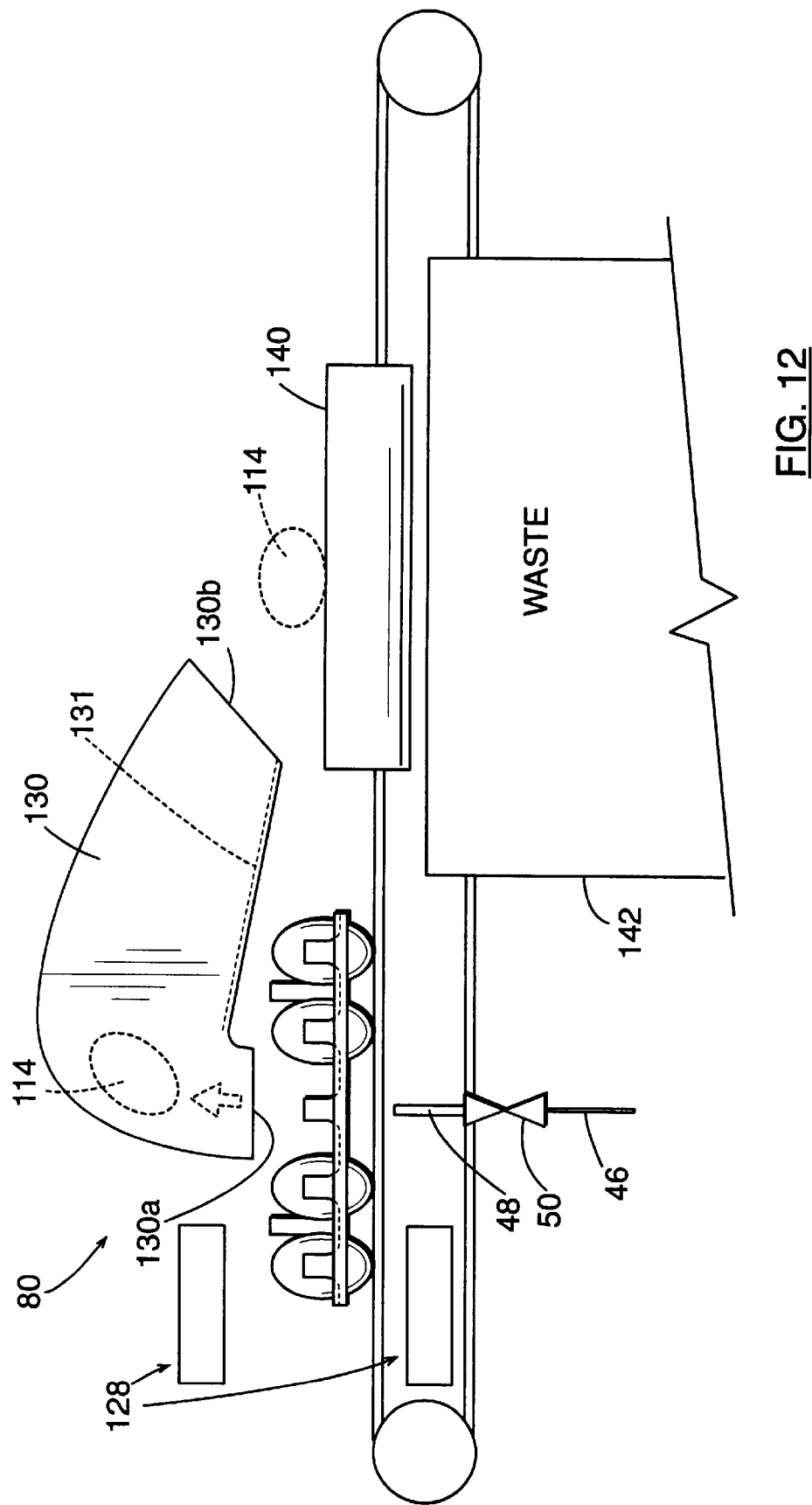
FIG. 12 is a side elevation view of the apparatus of FIG. 11.

Referring now to FIGS. 11 and 12, an apparatus 80 for removing selected eggs from an egg flat 10 according to another embodiment of the present invention is illustrated. The illustrated apparatus 80 includes an egg identification system 128 for identifying eggs to be removed from the egg flat. The egg identification system 128 may be configured to identify clear eggs as described above (28, FIG. 3), or may be configured to identify eggs having other characteristics. The apparatus 80 also includes an egg ejection system 129, responsive to the egg identification system 128, for ejecting identified eggs from the egg flat 10 into a disposal receptacle 142 positioned adjacent the egg flat 10 via a duct 130, as illustrated.

The duct 130 includes an inlet 130a positioned above the eggs 14 in the egg flat 10 and an opposite outlet 130b that is configured to deposit ejected eggs 114 onto a conveyor system 140 that transports the ejected eggs 114 to a disposal receptacle 142. The illustrated duct 130 includes a sloping floor 131 that allows eggs to roll onto the conveyor system 140 and that serves to prevent broken egg material from dripping or falling onto the egg flat 10. The illustrated duct 130 also includes side walls 132 that help channel and direct the ejected eggs.

An egg may be removed via the apparatus 80 illustrated in FIGS. 11 and 12 via a stream of air applied to an end of the egg as described in detail above. As illustrated in FIG. 12, a nozzle 48 that is positioned adjacent an end of a respective egg 14 within a respective row of an egg flat 10 passing thereover is configured to direct a stream of pressurized air onto the end of an identified egg so as to eject the egg upwardly into the duct inlet 130a and through the duct 130. As illustrated, ejected eggs 114 exit the duct 130 via the duct outlet 130b. In the illustrated embodiment, eggs 114 exiting from the duct outlet 130b are transported to a disposal receptacle 142 via a conveyor system 140. Conveyor systems are well known and need not be described further herein.

Figure 13:
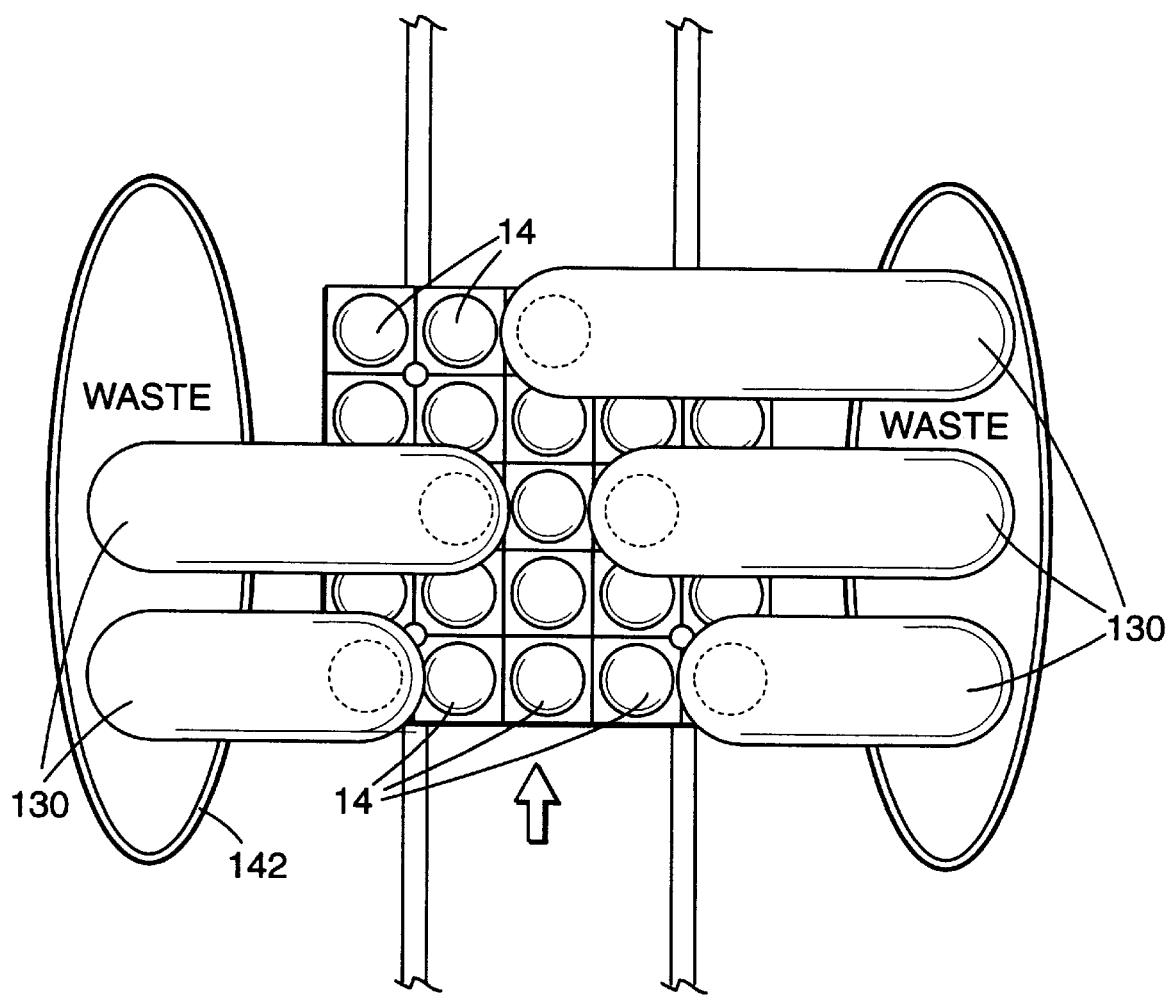
FIG. 13 is a top plan view of an egg flat passing through an apparatus according to an embodiment of the present invention wherein a separate duct is positioned above a respective egg within a row of an egg flat.
Figure 14:
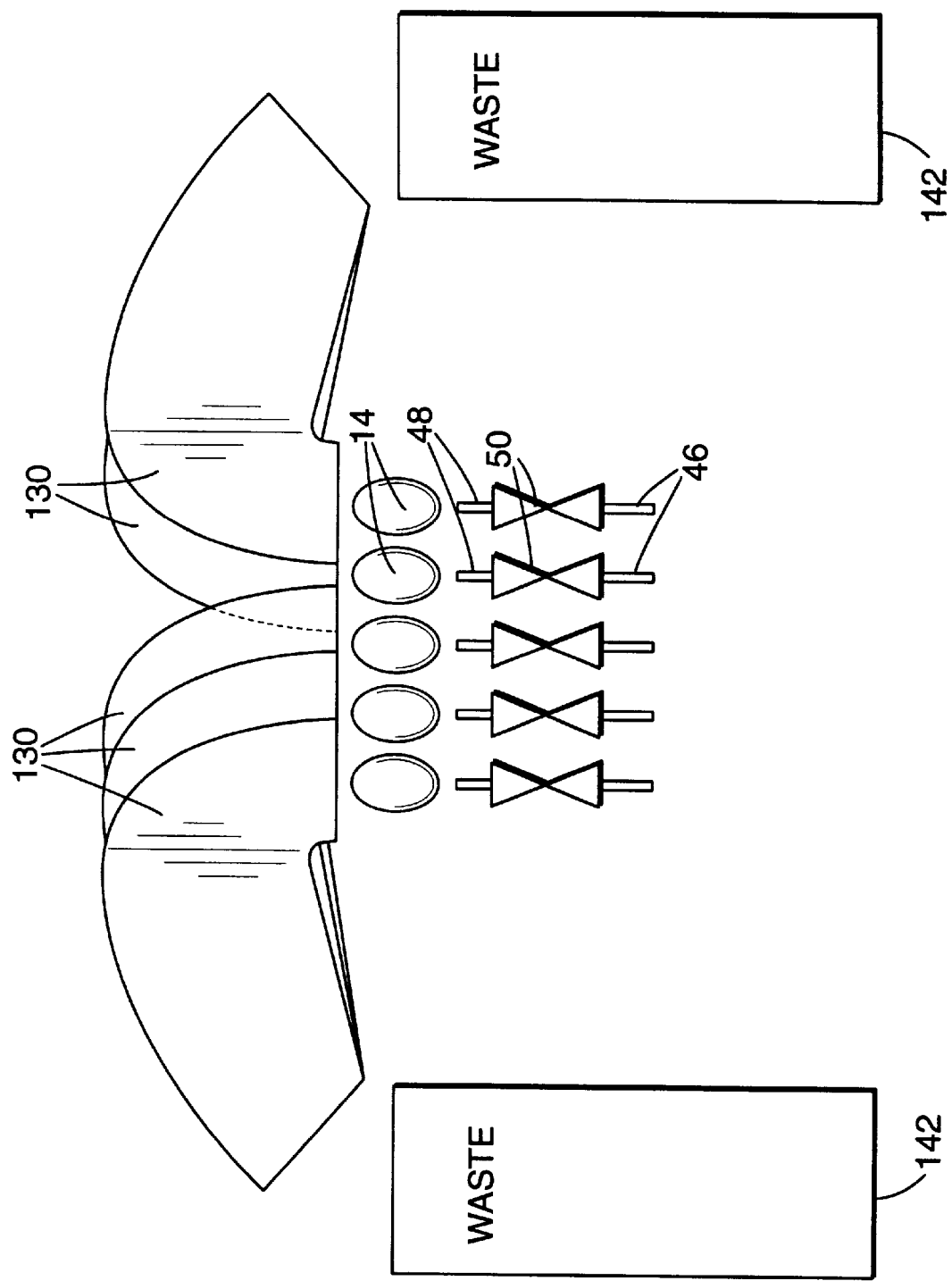
FIG. 14 is a side elevation view of the apparatus of FIG. 12.

As illustrated in FIGS. 13 and 14, a plurality of ducts 130 may be utilized. In the illustrated embodiment a separate duct 130 is positioned above a respective egg within a row of the egg flat 10. Each duct 130 is configured to direct an egg into a disposal receptacle positioned adjacent the moving egg flat 10.

According to another embodiment of the present invention, in lieu of a stream of air, a vacuum may be applied to the ducts 130 illustrated in FIGS. 11–14 so that an egg is pulled upwardly into and through a duct 130. Vacuum systems for pulling a vacuum within a duct are well known and need not be described further herein.

Preferably, the illustrated ducts 130 in FIGS. 11–14 are configured such that an egg can pass therethrough without breaking. Furthermore, it is preferred that ducts 130 used in accordance with the present invention are configured to prevent ejected eggs from falling back down upon egg flats 10 passing therebeneath. For example, it is preferred that each duct 130 have a smooth, sloping configuration such that any contact with an egg is gentle and such that an egg is gently redirected from a vertical motion to a horizontal motion. Ducts according to the present invention may have various orientations and configurations and are not limited to the illustrated embodiments.

The use of one or more ducts in accordance with the present invention is advantageous because a duct can help dampen the noise created by an air ejection system and can limit the possibility that empty shells are blown high in the air above an intended receptacle.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of removing poultry eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, the method comprising the steps of:

selecting an egg to be removed;

releasing the selected egg from a stuck condition within the egg flat prior to the step of ejecting the selected egg from the egg flat; and ejecting the selected egg from the egg flat into a stationary receptacle located above the moving egg flat.

2. A method according to claim 1 wherein the step of ejecting the selected egg from the egg flat comprises applying an upwardly-directed first stream of air to the first end of the selected egg for a first predetermined period of time.

3. A method according to claim 1 wherein the step of selecting an egg to be removed comprises the step of identifying a clear egg.

4. A method according to claim 3 wherein the step of identifying a clear egg comprises the steps of:

providing a plurality of pairs of light sources and corresponding light detectors in opposite facing relation to one another;

passing the egg flat between the light sources and light detectors such that each row in the egg flat is positioned between a corresponding pair of the plurality of light sources and light detectors; and detecting light that passes through each egg in each row of eggs from a light source with a corresponding light detector.

5. A method according to claim 1 wherein the stationary receptacle is positioned above the selected egg when the first stream of air is applied to the first end of the selected egg.

6. A method according to claim 1 wherein the step of ejecting the selected egg from the egg flat further comprises the step of applying a second stream of air to the selected egg along a direction substantially transverse to the first stream of air for a second predetermined period of time.

7. A method according to claim 6 wherein the second predetermined period of time is between about 30 milliseconds and about 100 milliseconds.

8. A method according to claim 1 wherein the step of releasing the selected egg from a stuck condition within the egg flat comprises the steps of:

applying a third stream of air to the first end of the selected egg for a third predetermined period of time; and applying a force to the selected egg in a direction counter to the third stream of air to limit vertical movement of the selected egg.

9. A method according to claim 1 wherein the first predetermined period of time is between about 30 milliseconds and about 100 milliseconds.

10. A method of removing poultry eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, the method comprising the steps of:

selecting an egg to be removed; and ejecting the selected egg from the egg flat into a stationary receptacle located above the moving egg flat comprising the steps of:

applying an upwardly-directed first stream of air to the first end of the selected egg for a first predetermined period of time; and applying a second stream of air to the selected egg after the first stream of air has been applied to the selected egg first end, and wherein the second stream of air is applied to the selected egg along a direction substantially transverse to the first stream of air for a second predetermined period of time.

11. A method according to claim 10 wherein the step of selecting an egg to be removed comprises the step of identifying a clear egg.

12. A method according to claim 11 wherein the step of identifying a clear egg comprises the steps of:

providing a plurality of pairs of light sources and corresponding light detectors in opposite facing relation to one another;

passing the egg flat between the light sources and light detectors such that each row in the egg flat is positioned between a corresponding pair of the plurality of light sources and light detectors; and detecting light that passes through each egg in each row of eggs from a light source with a corresponding light detector.

13. A method according to claim 10 wherein the stationary receptacle is positioned above the selected egg when the first stream of air is applied to the first end of the selected egg.

14. A method according to claim 10 further comprising the step of releasing the selected egg from a stuck condition within the egg flat prior to the step of ejecting the selected egg from the egg flat.

15. A method according to claim 14 wherein the step of releasing the selected egg from a stuck condition within the egg flat comprises the steps of:

applying a third stream of air to the first end of the selected egg for a third predetermined period of time; and applying a force to the selected egg in a direction counter to the third stream of air to limit vertical movement of the selected egg.

16. A method according to claim 10 wherein the each of the first and second predetermined periods of time is between about 30 milliseconds and about 100 milliseconds.

17. A method of removing clear poultry eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, the method comprising the steps of:

selecting a clear egg to be removed, comprising the steps of:

providing a plurality of pairs of light sources and corresponding light detectors in opposite facing relation to one another;

passing the egg flat between the light sources and light detectors such that each row in the egg flat is positioned between a corresponding pair of the plurality of light sources and light detectors; and detecting light that passes through each egg in each row of eggs from a light source with a corresponding light detector; and ejecting the selected clear egg from the egg flat into a stationary receptacle located above the moving egg flat by applying an upwardly-directed first stream of air to the first end of the selected clear egg for a first predetermined period of time, and by applying a second stream of air to the selected egg along a direction substantially transverse to the first stream of air for a second predetermined period of time.

18. A method according to claim 17 wherein the stationary receptacle is positioned above the selected egg when the first stream of air is applied to the first end of the selected egg.

19. A method according to claim 17 further comprising the step of releasing the selected egg from a stuck condition within the egg flat prior to the step of ejecting the selected egg from the egg flat.

20. A method according to claim 19 wherein the step of releasing the selected egg from a stuck condition within the egg flat comprises the steps of:

limiting vertical movement of the selected egg; and applying a third stream of air to the first end of the selected egg for a third predetermined period of time.

21. A method according to claim 17 wherein the first predetermined period of time is between about 30 milliseconds and about 100 milliseconds.

22. A method according to claim 17 wherein the second predetermined period of time is between about 30 milliseconds and about 100 milliseconds.

23. A method of removing eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, the method comprising the steps of:

selecting at least one egg to be removed from the egg flat;

releasing the selected at least one egg from a stuck condition within the egg flat prior to the step of ejecting the selected at least one egg from the egg flat; and ejecting the selected at least one egg from the egg flat into a receptacle positioned adjacent the egg flat via at least one duct positioned above the selected at least one egg.

24. A method according to claim 23 wherein the step of ejecting the selected at least one egg from the egg flat comprises applying an upwardly-directed first stream of air to the first end of the selected at least one egg for a first predetermined period of time.

25. A method according to claim 23 wherein the step of ejecting the selected at least one egg from the egg flat comprises applying a vacuum to the at least one duct so as to pull the selected at least one egg upwardly from the egg flat and through the duct into the receptacle.

26. A method according to claim 23 wherein the step of selecting at least one egg to be removed comprises the step of identifying a clear egg.

27. A method according to claim 26 wherein the step of identifying a clear egg comprises the steps of:

providing a plurality of pairs of light sources and corresponding light detectors in opposite facing relation to one another;

passing the egg flat between the light sources and light detectors such that each row in the egg flat is positioned between a corresponding pair of the plurality of light sources and light detectors; and detecting light that passes through each egg in each row of eggs from a light source with a corresponding light detector.

28. A method according to claim 23 wherein the step of releasing the selected at least one egg from a stuck condition within the egg flat comprises the steps of:

applying a second stream of air to the first end of the selected at least one egg for a second predetermined period of time; and applying a force to the selected at least one egg in a direction counter to the second stream of air to limit vertical movement of the selected egg.

29. An apparatus for removing eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, comprising:

means for selecting an egg to be removed;

means for releasing the selected egg from a stuck condition within the egg flat prior to the step of ejecting the selected egg from the egg flat; and means for ejecting the selected egg from the egg flat into a stationary receptacle located above the moving egg flat.

30. An apparatus according to claim 29 wherein the means for ejecting the selected egg from the egg flat comprises means for applying a first stream of air to the first end of the selected egg for a first predetermined period of time.

31. An apparatus according to claim 30 further comprising means for maintaining a pressure of the first stream of air substantially constant.

32. An apparatus according to claim 29 wherein the means for selecting an egg to be removed comprises means for identifying a clear egg.

33. An apparatus according to claim 32 wherein the means for identifying a clear egg comprises:

a plurality of pairs of light sources and corresponding light detectors in opposite facing relation to one another;

means for passing the egg flat between the light sources and light detectors such that each row in the egg flat is positioned between a corresponding pair of the plurality of light sources and light detectors; and means for detecting light that passes through each egg in each row of eggs from a light source with a corresponding light detector.

34. An apparatus according to claim 29 wherein the stationary receptacle is positioned above the selected egg when the first stream of air is applied to the first end of the selected egg.

35. An apparatus according to claim 29 wherein the means for ejecting the selected egg from the egg flat further comprises means for applying a second stream of air to the selected egg after the first stream of air has been applied to the selected egg first end, and wherein the second stream of air is applied to the selected egg along a direction substantially transverse to the first stream of air for a second predetermined period of time.

36. An apparatus according to claim 35 wherein the second predetermined period of time is between about 30 milliseconds and about 100 milliseconds.

37. An apparatus according to claim 29 wherein the means for releasing the selected egg from a stuck condition within the egg flat comprises:

means for limiting vertical movement of the selected egg; and means for applying a third stream of air to the first end of the selected egg for a third predetermined period of time.

38. An apparatus according to claim 30 wherein the first predetermined period of time is between about 30 milliseconds and about 100 milliseconds.

39. An apparatus for removing clear poultry eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, comprising:

a clear egg identification system, comprising:

a plurality of light sources positioned on one side of the egg flat; and a corresponding plurality of light detectors positioned on a side of the egg flat opposite the light source, wherein the light detectors are configured to identify clear eggs based upon an amount of light from a respective light source that passes through an egg;

an egg flat transport system for transporting the egg flat between the light sources and light detectors such that each egg within a row is positioned between a light source and a corresponding light detector;

means for releasing an egg from a stuck condition within the egg flat; and a clear egg ejection system, responsive to the clear egg identification system, for ejecting identified clear eggs from the egg flat into a stationary receptacle located above the moving egg flat.

40. An apparatus according to claim 39 wherein the clear egg ejection system comprises:

a supply of pressurized air;

a first plurality of air lines in fluid communication with the pressurized air supply, wherein each of the first plurality of air lines includes a first nozzle positioned adjacent a first end of a respective egg within a respective row of the egg flat; and means for providing a first stream of air from the pressurized air supply through each of the first nozzles for a first predetermined period of time.

41. An apparatus according to claim 40 wherein the clear egg ejection system further comprises:

a second plurality of air lines in fluid communication with the pressurized air supply, wherein each of the second plurality of air lines includes a second nozzle positioned above the moving egg flat; and means for providing a second stream of air from the pressurized air supply through each of the second nozzles for a second predetermined period of time after the first stream of air has been applied to the selected egg first end, and wherein the second stream of air is applied to an ejected clear egg along a direction substantially transverse to the first stream of air for a second predetermined period of time.

42. An apparatus according to claim 41 wherein the second predetermined period of time is between about 30 milliseconds and about 100 milliseconds.

43. An apparatus according to claim 40 wherein the first predetermined period of time is between about 30 milliseconds and about 100 milliseconds.

44. An apparatus according to claim 39 wherein the clear egg ejection system further comprises means for maintaining each stream of air at a pressure that is substantially constant.

45. An apparatus according to claim 39 wherein each nozzle is positioned between about 0.25 inches and about 1.25 inches from a first end of a respective egg.

46. An apparatus according to claim 39 wherein each nozzle has an end portion with a diverging configuration.

47. An apparatus according to claim 39 wherein the means for releasing an egg from a stuck condition within the egg flat comprises:

means for limiting vertical movement of the egg; and means for applying a third stream of air to the first end of the egg for a third predetermined period of time.

48. An apparatus for removing selected eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, comprising:

an egg identification system for identifying eggs to be removed from the egg flat;

means for releasing an egg from a stuck condition within the egg flat; and an egg ejection system, responsive to the egg identification system, for ejecting identified eggs from the egg flat into a receptacle positioned adjacent the egg flat via at least one duct, wherein the at least one duct includes an inlet positioned above the identified eggs and an opposite outlet in communication with the receptacle.

49. An apparatus according to claim 48 wherein the egg ejection system further comprises a conveyor system configured to transport ejected eggs from the outlet of the at least one duct to the receptacle.

50. An apparatus according to claim 48 wherein the egg ejection system comprises:

a supply of pressurized air;

a plurality of air lines in fluid communication with the pressurized air supply, wherein each of the plurality of air lines includes a nozzle positioned adjacent a first end of a respective egg within a respective row of the egg flat; and means for providing an upwardly-directed stream of air r from the pressurized air supply through each of the first nozzles for a first predetermined period of time such that an egg moves upwardly from the egg flat and through the at least one duct and into the receptacle.

51. An apparatus according to claim 48 wherein the at least one duct comprises a plurality of ducts, and wherein each duct is positioned above a respective egg within a row of the egg flat.

52. An apparatus according to claim 48 wherein the egg ejection system further comprises means for maintaining each stream of air at a pressure that is substantially constant.

53. An apparatus according to claim 48 wherein each nozzle is positioned between about 0.25 inches and about 1.25 inches from a first end of a respective egg.

54. An apparatus according to claim 48 wherein each nozzle has an end portion with a diverging configuration.

55. An apparatus according to claim 48 wherein the means for releasing an egg from a stuck condition within the egg flat comprises:

means for limiting vertical movement of the egg; and means for applying a stream of air to the first end of the egg for a predetermined period of time.

56. A method of removing clear poultry eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, the method comprising the steps of:

selecting a clear egg to be removed, comprising the steps of:

providing a plurality of pairs of light sources and corresponding light detectors in opposite facing relation to one another;

passing the egg flat between the light sources and light detectors such that each row in the egg flat is positioned between a corresponding pair of the plurality of light sources and light detectors; and detecting light that passes through each egg in each row of eggs from a light source with a corresponding light detector;

releasing the selected egg from a stuck condition within the egg flat; and ejecting the selected clear egg from the egg flat into a stationary receptacle located above the moving egg flat by applying an upwardly-directed first stream of air to the first end of the selected clear egg for a first predetermined period of time.

57. A method according to claim 56 wherein the step of ejecting the selected egg from the egg flat further comprises the step of applying a second stream of air to the selected egg along a direction substantially transverse to the first stream of air for a second predetermined period of time.

58. A method according to claim 57 wherein the second predetermined period of time is between about 30 milliseconds and about 100 milliseconds.

59. A method according to claim 56 wherein the stationary receptacle is positioned above the selected egg when the first stream of air is applied to the first end of the selected egg.

60. A method according to claim 56 wherein the step of releasing the selected egg from a stuck condition within the egg flat comprises the steps of:

limiting vertical movement of the selected egg; and applying a third stream of air to the first end of the selected egg for a third predetermined period of time.

61. A method according to claim 56 wherein the first predetermined period of time is between about 30 milliseconds and about 100 milliseconds.

62. An apparatus for removing eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, comprising:

means for selecting an egg to be removed; and means for ejecting the selected egg from the egg flat into a stationary receptacle located above the moving egg flat, comprising:

means for applying a first stream of air to the first end of the selected egg for a first predetermined period of time; and means for applying a second stream of air to the selected egg after the first stream of air has been applied to the selected egg first end, and wherein the second stream of air is applied to the selected egg along a direction substantially transverse to the first stream of air for a second predetermined period of time.

63. An apparatus according to claim 62 wherein the means for selecting an egg to be removed comprises means for identifying a clear egg.

64. An apparatus according to claim 63 wherein the means for identifying a clear egg comprises:
- a plurality of pairs of light sources and corresponding light detectors in opposite facing relation to one another;
- means for passing the egg flat between the light sources and light detectors such that each row in the egg flat is positioned between a corresponding pair of the plurality of light sources and light detectors; and
- means for detecting light that passes through each egg in each row of eggs from a light source with a corresponding light detector.

65. An apparatus according to claim 62 wherein the stationary receptacle is positioned above the selected egg when the first stream of air is applied to the first end of the selected egg.

66. An apparatus according to claim 62 further comprising means for releasing the selected egg from a stuck condition within the egg flat prior to the step of ejecting the selected egg from the egg flat.

67. An apparatus according to claim 66 wherein the means for releasing the selected egg from a stuck condition within the egg flat comprises:
- means for limiting vertical movement of the selected egg; and
- means for applying a third stream of air to the first end of the selected egg for a third predetermined period of time.

68. An apparatus according to claim 62 wherein the first predetermined period of time is between about 30 milliseconds and about 100 milliseconds.

69. An apparatus according to claim 62 wherein the second predetermined period of time is between about 30 milliseconds and about 100 milliseconds.

70. An apparatus according to claim 62 further comprising means for maintaining a pressure of the first stream of air substantially constant.

71. An apparatus for removing clear poultry eggs from an egg flat that is moving along a substantially horizontal direction, wherein the egg flat comprises a plurality of rows of apertures, and wherein each aperture is configured to receive a first end of a respective egg so as to support the respective egg in a substantially vertical position, comprising:
- a clear egg identification system, comprising:
  - a plurality of light sources positioned on one side of the egg flat; and
  - a corresponding plurality of light detectors positioned on a side of the egg flat opposite the light source, wherein the light detectors are configured to identify clear eggs based upon an amount of light from a respective light source that passes through an egg;
- an egg flat transport system for transporting the egg flat between the light sources and light detectors such that each egg within a row is positioned between a light source and a corresponding light detector; and
- a clear egg ejection system, responsive to the clear egg identification system, for ejecting identified clear eggs from the egg flat into a stationary receptacle located above the moving egg flat, comprising:
  - a supply of pressurized air;
  - a first plurality of air lines in fluid communication with the pressurized air supply, wherein each of the first plurality of air lines includes a first nozzle positioned adjacent a first end of a respective egg within a respective row of the egg flat;
  - means for providing a first stream of air from the pressurized air supply through each of the first nozzles for a first predetermined period of time;
  - a second plurality of air lines in fluid communication with the pressurized air supply, wherein each of the second plurality of air lines includes a second nozzle positioned above the moving egg flat; and
  - means for providing a second stream of air from the pressurized air supply through each of the second nozzles for a second predetermined period of time after the first stream of air has been applied to the selected egg first end, and wherein the second stream of air is applied to an ejected clear egg along a direction substantially transverse to the first stream of air for a second predetermined period of time.

72. An apparatus according to claim 71 wherein the clear egg ejection system further comprises means for maintaining each stream of air at a pressure that is substantially constant.

73. An apparatus according to claim 71 wherein each nozzle is positioned between about 0.25 inches and about 1.25 inches from a first end of a respective egg.

74. An apparatus according to claim 71 wherein each nozzle has an end portion with a diverging configuration.

75. An apparatus according to claim 71 further comprising means for releasing an egg from a stuck condition within the egg flat.

76. An apparatus according to claim 71 wherein the means for releasing an egg from a stuck condition within the egg flat comprises:
- means for limiting vertical movement of the egg; and
- means for applying a third stream of air to the first end of the egg for a third predetermined period of time.

77. An apparatus according to claim 71 wherein the first predetermined period of time is between about 30 milliseconds and about 100 milliseconds.

78. An apparatus according to claim 71 wherein the second predetermined period of time is between about 30 milliseconds and about 100 milliseconds.

* * * * *

UNITED STATES PATENT AND TRADEMARK OFFICE
CERTIFICATE OF CORRECTION

PATENT NO. : 6,145,668
DATED : November 14, 2000
INVENTOR(S) : DePauw et al.

It is certified that error appears in the above-identified patent and that said Letters Patent is hereby corrected as shown below:

<u>Column 5,</u>
Line 36 should read -- indicated as $D_1$ in FIG. 3. --

<u>Column 15,</u>
Line 42 should read -- means for providing an upwardly-directed stream of air --

Signed and Sealed this

Seventh Day of May, 2002

*Attest:*

JAMES E. ROGAN
*Attesting Officer*     *Director of the United States Patent and Trademark Office*